US012692224B2

(12) United States Patent
Kukkonen

(10) Patent No.: US 12,692,224 B2
(45) Date of Patent: Jul. 28, 2026

(54) METHOD FOR PREPARING ARYLVINYLSULPHONES

(71) Applicant: KEMIRA OYJ, Helsinki (FI)

(72) Inventor: Viktor Kukkonen, Espoo (FI)

(73) Assignee: KEMIRA OYJ, Helsinki (FI)

( * ) Notice: Subject to any disclaimer, the term of this patent is extended or adjusted under 35 U.S.C. 154(b) by 564 days.

(21) Appl. No.: 18/035,535

(22) PCT Filed: Nov. 5, 2021

(86) PCT No.: PCT/EP2021/080834
§ 371 (c)(1),
(2) Date: May 5, 2023

(87) PCT Pub. No.: WO2022/096682
PCT Pub. Date: May 12, 2022

(65) Prior Publication Data

US 2023/0391718 A1 Dec. 7, 2023

(30) Foreign Application Priority Data

Nov. 5, 2020 (FI) ..................................... 20206108

(51) Int. Cl.
*C07C 315/04* (2006.01)
*B01J 31/22* (2006.01)

(52) U.S. Cl.
CPC ......... *C07C 315/04* (2013.01); *B01J 31/2252* (2013.01)

(58) Field of Classification Search
USPC ............................................................ 568/28
See application file for complete search history.

(56) References Cited

U.S. PATENT DOCUMENTS

| | | | |
|---|---|---|---|
| 4,049,695 | A | 9/1977 | Burk et al. |
| 2004/0204556 | A1 | 10/2004 | Matyjaszewski et al. |
| 2020/0190026 | A1 | 6/2020 | Aaltonen et al. |

FOREIGN PATENT DOCUMENTS

| | | |
|---|---|---|
| EP | 3450623 | 3/2019 |
| JP | S5799565 | 6/1982 |
| JP | H0586298 | 4/1993 |
| WO | 2019042985 | 3/2019 |
| WO | 2020094917 | 5/2020 |

OTHER PUBLICATIONS

Asscher M, Vofsi D. 954. Chlorine-activation by redox-transfer. Part IV. The addition of sulphonyl chlorides to vinylic monomers and other olefins. Journal of the Chemical Society (Resumed). 1964:4962-71.

*Primary Examiner* — Ana Z Muresan
(74) *Attorney, Agent, or Firm* — Robin L. Teskin; Baker, Donelson, Bearman, Caldwell & Berkowitz PC

(57) ABSTRACT

The invention relates to a method of preparing arylvinylsulphones. The method comprises forming o a first reaction mixture comprising a catalyst complex of Cu(I)halide and a ligand, wherein the ligand is selected from mono-, bi- or polydentate amine ligands and further comprises an organic sulphonate; a reactive solvent selected from (meth)acrylonitrile or alkyl (meth)acrylate; and an aryl sulfonyl halide reactant. A reaction is allowed to proceed in the first reaction mixture at an elevated temperature, whereby an intermediate product is obtained. The unreacted reactive solvent is separated from the first reaction mixture, and the intermediate product is dissolved to a low polarity solvent to form a second reaction mixture. A base is added to the second reaction mixture, wherein the intermediate product undergoes a base-catalyzed elimination of the halogen atom from the intermediate product to form the compound according to Formula (I), preferably under cooling. Finally, the desired compound is separated from the second reaction mixture.

29 Claims, No Drawings

METHOD FOR PREPARING ARYLVINYLSULPHONES

RELATED APPLICATIONS

This application is a U.S. National Phase application of Int'l Appl. No. PCT/EP2021/080834, filed Nov. 5, 2021, which claims priority to Finnish Appl. No. 20206108, filed Nov. 5, 2020, each of which are incorporated herein by reference in their entireties.

The present invention relates to a method of preparing compounds of formula (I).

BACKGROUND

Arylvinylsulphones have various industrial uses. For example, 3-(arylsulphonyl)propene nitriles can be used as biocides in industrial processes, as disclosed in WO 2019/042984 and WO 2019/042985.

A number of methods exist for preparing arylvinylsulphones. However, many of these methods employ solvents that are environmentally harmful, volatile, flammable and/or scarcely available, such as acetonitrile or sulfolane. Furthermore, the existing processes comprise number of steps, which increases the complexity of the processes. Furthermore, there are only limited possibilities to recirculate any of the used chemicals within the process. Consequently, there is a need for new effective method for preparing arylvinylsulphones, especially arylsulphonylpropene nitriles.

An object of the present invention is to minimise or possibly even eliminate the disadvantages existing in the prior art.

A further object of the present invention is to provide an efficient and simple method for preparing arylvinylsulphones.

Another object of the present invention is to provide a method for preparing arylvinylsulphones, preferably arylsulphonylpropene nitriles, where at least some of the chemicals can be recirculated within the process.

A further object of the present invention is to provide a safe method for preparing arylvinylsulphones,

SUMMARY OF THE INVENTION

These objects are attained with the invention having the characteristics presented below in the characterising parts of the independent claims.

Some preferred embodiments of the invention are presented in the dependent claims.

The embodiments mentioned in this text relate, where applicable, to all aspects of the invention, even if this is not always separately mentioned.

Accordingly, the present invention provides a method for preparing a compound of formula (I)

(I)

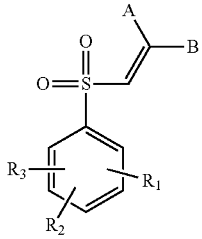

where

R1, R2, and R3 independently represent a hydrogen atom; a halogen atom; a hydroxy group, an alkyl group; a hydroxy alkyl group; a haloalkyl group; an alkoxy group having 1 to 4 carbon atoms; an amino group; an alkylamino group or an acylamido group having 1 to 10 carbon atoms;

A represents a hydrogen atom or a C1-C5 alkyl group;

B represents a nitrile group; a carboxylic acid group, a carboxylic acid ester group or a carboxylic acid amide group.

The method comprises steps of- (a) forming a first reaction mixture comprising
  - a catalyst complex comprising Cu(I) and a ligand, wherein the ligand is selected from mono-, bi- or polydentate amine ligands;
  - an organic sulphonate counterion;
  - a reactive solvent selected from (meth)acrylonitrile or alkyl (meth)acrylate; and
  - an aryl sulfonyl halide reactant;

(b) allowing a reaction to proceed in the first reaction mixture at an elevated temperature, whereby an intermediate product is obtained;

(c) separating the unreacted reactive solvent from the first reaction mixture, and dissolving the intermediate product to a low polarity solvent to form a second reaction mixture;

(d) adding a base to the second reaction mixture, wherein the intermediate product undergoes a base-catalyzed elimination of the halogen atom from the intermediate product to form the compound according to Formula (I), preferably under cooling; and (e) separating the compound according to Formula (I) from the second reaction mixture.

In one arrangement, step (a) comprises:

(i) forming a pre-reaction mixture comprising
  - a catalyst complex of the Cu(I) and the ligand;
  - an organic sulphonate counterion;
  - a reactive solvent selected from (meth)acrylonitrile or alkyl (meth)acrylate; and (ii) adding an amount of aryl sulfonyl halide to the pre-reaction mixture to form the first reaction mixture.

In a further aspect, the present invention provides a method for preparing a compound of formula (I)

(I)

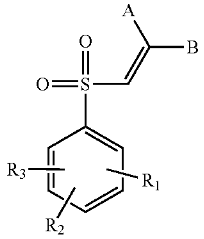

where

R1, R2, and R3 independently represent a hydrogen atom; a halogen atom; a hydroxy group, an alkyl group; a hydroxy alkyl group; a haloalkyl group; an alkoxy group having 1 to 4 carbon atoms; an amino group; an alkylamino group or an acylamido group having 1 to 10 carbon atoms;

A represents a hydrogen atom; a C1-C5 alkyl group; or an alkoxycarbonyl group;

B represents a nitrile group; a carboxylic acid group, a carboxylic acid ester group or a carboxylic acid amide group;

the method comprising steps of- (1) forming a pre-reaction mixture comprising a catalyst complex of Cu(I)halide and a ligand, wherein the ligand is selected from mono-, bi- or polydentate amine ligands; aryl sulphonates; and alkyl sulphonates; and a reactive solvent selected from (meth)acrylonitrile or alkyl (meth)acrylate;

(2) adding an amount of aryl sulfonyl halide to the pre-reaction mixture to form a first reaction mixture;

(3) allowing a reaction to proceed in the first reaction mixture at an elevated temperature, whereby an intermediate product is obtained, (4) separating the unreacted reactive solvent from the first reaction mixture, and dissolving the intermediate product to a low polarity solvent to form a second reaction mixture;

(5) adding a base to the second reaction mixture, wherein the intermediate product undergoes a base-catalyzed elimination of the halogen atom from the intermediate product to form the compound according to Formula (I), preferably under cooling; and (6) separating the compound according to Formula (I) from the second reaction mixture.

Now it has been surprisingly found that by using the method of the present invention it is possible to prepare arylvinylsulphones of formula (I), especially arylsulphonylpropene nitriles, by using easily available, relatively inexpensive, and safe starting materials and reagents. Furthermore, the invention open possibilities for recirculating at least a part of the reagents within the process, and thus reduces the amount of chemical waste produced and improves the overall process economy.

It has been found that catalyst complexes which include as a counterion an organic sulphonate are superior to comparable catalyst complexes which have a halide counterion such as a chloride counterion. Without wishing to be bound by theory, it is thought that the presence of halide counterions can contribute to the formation of undesirable polynuclear catalyst complexes which may increase impurity production in the preparation of compounds according to formula (I).

In the present context the term “catalyst complex” is used to denote a combination of individual atoms, groups of atoms, or molecules that have in the presence of a counterion a total net charge of zero that is able to catalyze a chemical reaction. The catalyst complex itself comprises a Cu(I) as the central atom or molecule as well as a ligand. A non-limiting example of such a catalyst complex is the Cu(I) methylmorpholine—complex in the presence of methane sulphonate or toluene sulphonate.

The method according to the present invention is especially suitable for preparing compounds of formula (I)

(I)

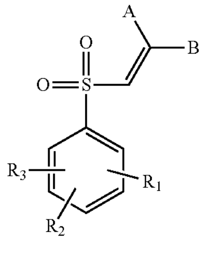

where

R1, R2, and R3 independently represent a hydrogen atom; a halogen atom; a hydroxy group, an alkyl group; a hydroxy alkyl group; a haloalkyl group; an alkoxy group having 1 to 4 carbon atoms; an amino group; an alkylamino group or an acylamido group having 1 to 10 carbon atoms;

A represents a hydrogen atom or a C1-C5 alkyl group; and

B represents a nitrile group; a carboxylic acid group, a carboxylic acid ester group or a carboxylic acid amide group.

In one embodiment of the invention, R1 in formula (I) represents a hydrogen atom, an alkyl group comprising 1 to 4 carbon atoms or an alkoxy group having 1 to 4 carbon atoms. R1 can be, for example, a methyl group, an ethyl group, a propyl group; a butyl group, a methoxy group, an ethoxy group, a propoxy group, an isopropoxy group, a n-butoxy group, or a tertiary butoxy group. Preferably, R1 represents a methyl group in the 4-position.

R2 and R3 in formula (I) represent independently from each other and independently from R1 a hydrogen atom, an alkyl group comprising 1 to 4 carbon atoms or an alkoxy group having 1 to 4 carbon atoms. R2 and/or R3 may be, for example, a methyl group, an ethyl group, a propyl group, a butyl group, a methoxy group, an ethoxy group, a propoxy group, an isopropoxy group, a n-butoxy group, or a tertiary butoxy group. Preferably, both R2 and R3 represent a hydrogen atom.

According to one embodiment R1, R2 and/or R3 in formula (I) may represent independently from each other a halogen atom, such as chlorine, fluorine or bromine; a hydroxy group; a hydroxy alkyl group preferably comprising 1-4 carbon atoms; a haloalkyl group preferably comprising 1-4 carbon atoms and/or fluoro-substituents, such as trifluoromethyl; an amino group; an alkylamino group having 1 to 10 carbon atoms; or an acylamido group having 1 to 10 carbon atoms.

In a preferable embodiment R1 represents a methyl group in the 4-position of the aryl, and R2 and R3 both represent hydrogen.

According to one embodiment, group A in formula (I) represents a C1-C5 alkyl group or a hydrogen atom. Group A may be, for example, a methyl group, an ethyl group, a propyl group; a butyl group, or a pentyl group. Preferably, the group A is a hydrogen atom.

According to one embodiment, group B in formula (I) represents a nitrile group; a C1-C5 carboxylic acid group, a C1-C5 carboxylic acid ester group or a C1-C5 carboxylic acid amide group.

According to one embodiment of the invention the compound of formula (I) may be an arylsulphonylpropene nitrile. The compound of formula (I) may be selected from a group consisting of the compound according to formula (I) is 3-[(4-methylphenyl)sulphonyl]-2-propenenitrile, 3-phenylsulphonyl-2-propenenitrile, 3-[(4-fluorophenyl)sulphonyl]-2-propenenitrile, 3-[(2,4-dimethylphenyl)sulphonyl]-2-propenenitrile, 3-[(4-trifluormethylphenyl)-sulphonyl]-2-propenenitrile, 3-[(3,4-dimethylphenyl)sulphonyl]-2-propenenitrile, 3-(2,5-dimethylphenyl)sulphonyl-2-propenenitrile, 3-[(2,4,6-trimethylphenyl)sulphonyl]-2-propenenitrile, 3-(4-methoxyphenyl) sulphonyl-2-propenenitrile, methyl (3-[(4-methyl-phenyl)sulphonyl] prop-2-enate, 3-(4-acetylphenyl)sulphonyl-2-propenenitrile, and any of their isomers. According to one preferable embodiment of the present invention the compound according to formula (I) is selected from a group consisting of 3-[(4-methylphenyl)sulphonyl]-2-propenenitrile; 3-phenylsulphonyl-2-propenenitrile; 3-[(4-trifluormethylphenyl)-sulphonyl]-2-propenenitrile; 3-[(2,4,6-trimethylphenyl)sulphonyl]-2-propenenitrile; 3-(4-methoxyphenyl)sulphonyl-2-propenenitrile; 3-[(4-methylphenyl)sulphonyl]prop-2-enate; and any of their isomers. Preferably the compound of formula (I) may be 3-[(4-methylphenyl)sulphonyl]-2-propenenitrile.

In the method of the present invention a first reaction mixture is formed in solution form by mixing the components of the first reaction mixture with each other, preferably under an inert atmosphere, e.g. under a nitrogen atmosphere. According to one embodiment the first reaction mixture may be formed at a temperature of 15-40° C., preferably 20-30° C., more preferably 25-30° C. It is advantageous that the first reaction mixture may be formed in room temperature and no extensive heating is necessary. It has been observed that the components of the catalyst complex, i.e. Cu(I) and the ligand, effectively dissolve into the reactive solvent at the used temperature, thus simplifying the method. The forming of first reaction mixture is preferably free of any heating.

Typically, the Cu(I) is provided as a Cu(I) halide and may be, for example, Cu(I)chloride or Cu(I)bromide, preferably Cu(I)chloride. However, it is important to minimize the amount of halide added to reaction mixture to avoid the formation of unwanted polynuclear catalyst complexes. Preferably, the molar amount of halide ions in the first reaction mixture is no more than the molar amount of Cu(I). It is therefore preferred that no other sources of free halide ions are introduced if at all possible.

It is preferred that the organic sulphonate is supplied as a salt, preferably an ammonium salt, such as an N-methylmorpholinium salt.

The first reaction mixture comprises the catalyst complex of a Cu(I) and the ligand, as well as the organic sulphonate counterion and the reactive solvent. The ligand influences the reducing power of Cu(I). The ligand may be selected from monodentate amine ligands, bidentate amine ligands, polydentate amine ligands, aryl sulphonates, and alkyl sulphonates. Suitable monodentate, bidentate or polydentate amine ligands may be selected, for example, triethylamine, N-methylmorpholine, N, N, N', N'-tetramethylethylenediamine and N, N, N', N'', N''-pentamethyldiethylenetriamine. According to a preferable embodiment the ligand may be a bidentate amine ligand, for example morpholine or a substituted morpholine. The ligand may be an alkyl morpholine, such as N-methylmorpholine.

The counterion component comprises an organic sulphonate which may be an aryl sulphonate or an alkyl sulphonate selected from a group of methanesulphonate, ethanesulphonate, benzenesulphonate, 4-toluenesulphonate, and xylenesulphonate. Preferably the counterion is methanesulphonate or para-toluene sulphonate. The counterion may be present as an outer component of the catalyst complex because it is negatively charged and able to associate with a positively charged inner component comprising Cu(I), the ligand and optionally reactive solvent molecules.

The reactive solvent for the first reaction mixture may be selected from (meth)acrylonitrile or alkyl (meth)acrylates, such as methyl acrylate or methyl methacrylate. Preferably the reactive solvent may be acrylonitrile. According to one preferable embodiment of the present invention the first reaction mixture is free of all other solvents that the reactive solvent. This means that no other solvents than the reactive solvent are added to the first reaction mixture.

The catalyst complex of Cu(I) and the ligand, as defined above, is dissolved in the reactive solvent, whereby the first reaction mixture in solution form is obtained. The reactive solvent functions as a reactant, solvent and a co-ligand in the method according to the invention. The use of the reactive solvent, as defined, further improves the reducing power of Cu(I), and thus improves the efficiency of the reaction between the catalyst complex and the aryl sulphonyl halide, possibly even the yield of the reaction. The reactive solvent is preferably added in excess, which ensures the dissolution of the other components of the first reaction mixture. It has been found that the reactive solvent is able to dissolve the Cu(I)halide as well as the ligand effectively, even at room temperature. As noted above, no heating for forming the first reaction mixture is thus required. Furthermore, the excess reactive solvent enables exclusion of other solvents in the following process step when the reaction mixture is formed, as well as the desired reaction for obtaining the intermediate product for compound of formula (I). This simplifies the process and improves the conversion and/or yield of the process. However, only a small excess of reactive solvent may be added or needed.

The first reaction mixture may comprise particular material: it is possible that the catalyst complex may comprise minor amounts of Cu(II), which is not dissolved into the reactive solvent but remains in particle form. The amount of Cu(II) may be 0.5-5 mol-%, calculated from the total molar amount of copper in the first reaction mixture. Cu(II) ions may inhibit the polymerization reaction of the reactive solvent, such as acrylonitrile, in the reaction mixture in the successive method steps. This may be considered advantageous, as it can reduce the amount of undesired side reactions and formation of other compounds than the desired compound according to formula (I). The presence of Cu(II) is not necessary.

The aryl sulphonyl halide may be benzene sulphonyl halide, alkyl substituted benzene sulphonyl halide or halo-substituted benzene sulphonyl halide, such as toluene sulphonyl halide, xylene sulphonyl halide, 4-methoxybenzene sulphonyl halide or 4-chlorobenzene sulphonyl halide, preferably toluene sulphonyl chloride or toluene sulphonyl bromide, more preferably toluene sulphonyl chloride. For example, the aryl sulphonyl halide may be 4-toluene sulphonyl halide, preferably 4-toluene sulphonyl chloride or 4-toluene sulphonyl bromide, more preferably 4-toluene sulphonyl chloride. Aryl sulphonyl halide may be added in amount (in mol) of 0.2-0.5 equivalents, preferably 0.3-0.5 equivalents, more preferably 0.35-0.4 equivalents, relative to the amount (in mol) of the reactive solvent in the first reaction mixture. Aryl sulphonyl halide is dissolved in the first reaction mixture, under an endothermic process.

Preferably, the first reaction mixture does not contain any other solvent than the reactive solvent, i.e. the first reaction mixture is free of other solvents than the reactive solvent. The first reaction mixture may comprise the reactive solvent in amount (in mol) of at least 1.5 times, preferably at least 2 times, more preferably at least 3 times, of the amount (in mol) of the aryl sulphonyl halide. The molar amount of reactive solvent may be up to 5 times of the molar amount of the aryl sulphonyl halide.

In one arrangement, a pre-reaction mixture comprising the catalyst complex of the Cu(I) and the ligand, the organic sulphonate counterion and the reactive solvent is formed, to which the aryl sulfonyl halide is added to form the first reaction mixture. In another arrangement, no pre-reaction mixture is formed.

The aryl sulphonyl halide may be added to the pre-reaction mixture or first reaction mixture as one single dose, or as a plurality of successive doses, such as two, three or more successive doses. A continuous addition may also be possible. Preferably aryl sulphonyl halide is added as one single dose.

The amount of Cu(I)halide, preferably Cu(I)chloride in the first reaction mixture may be 2.5-30 mol-%, preferably 5-20 mol-%, more preferably 7.5-15 mol-% or 7.5-12.5 weight-%, calculated from the amount of the aryl sulphonyl halide in the first reaction mixture. The amount of the ligand, preferably alkyl sulphonate or aryl sulphonate, such as methanesulphonate, in the first reaction mixture may be 7-45 mol-% preferably 10-30 mol-%, more preferably 12.5-22.5 mol-%, calculated from the amount of the aryl sulphonyl halide in the first reaction mixture.

After the addition of the aryl sulphonyl halide to the first reaction mixture, and its dissolution, the reaction is allowed to proceed, preferably under inert atmosphere, e.g. nitrogen, at an elevated temperature, whereby an intermediate product is obtained. The reaction is a radical addition reaction. The reaction is preferably allowed to proceed at the elevated temperature, which is higher than the boiling point of the reactive solvent but below the boiling point of the reaction mixture. The reaction in the first reaction mixture may be allowed to proceed at the elevated temperature of 80-95° C., preferably 85-92° C., more preferably 88-90° C. The reaction is allowed to proceed until desired conversion of the intermediate product is obtained. The reaction time may be, for example 5-30 hours, preferably 10-24 hours or 18-24 hours.

After the reaction has proceeded to the desired conversion, the unreacted reactive solvent may be separated from the first reaction mixture. The reactive solvent may be separated by any suitable separation method, e.g. by distilling. According to one preferable embodiment, the reactive solvent may be separated from the first reaction mixture, optionally purified, and then recycled back in the process to the step (a). In this manner it is possible to reuse the unreacted reactive solvent for making of the first reaction mixture and effectively reduce the amount of chemical waste which is produced.

After the separation of the unreacted reactive solvent the obtained intermediate product is dissolved to a low polarity solvent to form a second reaction mixture. The intermediate product may be dissolved into a low polarity solvent, which has a relative polarity of <0.4, preferably <0.3, or even <0.25, to form the second reaction mixture. For purposes of the present context, the relative polarity values given, for example, in Reichardt, C. (ed.) and Welton, T. (ed.), "Solvents and Solvent Effects in Organic Chemistry", 4th Ed., 2011, Wiley-VCH Verlag GmbH & Co., Weinheim, Appendix A, or in other similar handbooks, can be used. The low polarity of the low polarity solvent reduces its ability to mix with water, which simplifies the separation of the intermediate product from the aqueous phase. The low polarity solvent may be considered hydrophobic. The low polarity solvent may be free of carboxyl or hydroxyl groups. Low polarity solvents suitable for use in the present invention may be selected, for example, from a group consisting of ethyl acetate, butyl acetate, tetrahydrofuran, dioxane and toluene. According to one preferable embodiment the low polarity solvent is ethyl acetate.

Cu(I) typically precipitates from the liquid phase of the second reaction mixture after the addition of the low polarity solvent. The Cu(I) precipitate may be easily separated from the liquid phase of the second reaction mixture that comprises the low polarity solvent and the intermediate product, e.g. by filtration.

After dissolving the intermediate product to the low polarity solvent for forming the second reaction mixture, and optional separation of Cu(I) precipitate, a base may be added to the second reaction mixture for elimination of the halogen atom from the intermediate product to form the compound according to formula (I). The intermediate product undergoes an elimination reaction in the presence of the base, where the halogen atom is removed from the intermediate product, i.e. a base-catalyzed elimination of the halogen atom, and the compound according to formula (I) is obtained. The base used may be an inorganic base, an organic base or a combination of an inorganic and organic base, preferably a combination of inorganic and organic base. The elimination reaction is exothermic, and therefore the base is preferably added, and the elimination reaction is allowed to proceed under cooling. According to one preferable embodiment the second reaction mixture is maintained in a temperature of 15-40° C., preferably 20-35° C., more preferably 20-25° C., during the elimination of halogen atom from the intermediate product.

The base may be added to the second reaction mixture relative to the amount of the dissolved intermediate in the second reaction mixture in an amount (in mol) of at least 0.9 equivalents, such as in the range 0.9 to 1.5, preferably 0.9 to 1.3 equivalents, most preferably around 1 equivalent; or at least 1 equivalent, or even at least 1.3 equivalents, although high amounts are less preferred.

According to one embodiment of the invention the base added to the second reaction mixture may be or comprise an inorganic base, preferably selected from a group comprising bicarbonates and carbonates of alkali metals and carbonates of alkaline earth metals or any mixtures thereof. For example, the inorganic base may be selected from sodium bicarbonate, sodium carbonate, potassium bicarbonate, potassium carbonate, lithium bicarbonate, lithium carbonate, cesium carbonate, calcium carbonate, magnesium carbonate or any mixture thereof. According to one preferable embodiment sodium bicarbonate or sodium carbonate is used as inorganic base.

According to one embodiment of the invention the base added to the second reaction mixture may be or comprise an organic base, preferably selected from trialkylamines, such as triethylamine, trimethylamine; N-methylmorpholine; N-methylpyrrolidine; N,N-diisopropylethylamine (Hünig's base); 1,4-diazabicyclo-[2.2.2]octane (DABCO); 1,8-diazabicyclo[5.4.0]undec-7-ene (DBU); or 1,5-diaza-bicyclo [4.3.0]non-5-ene (DBN), or any mixtures thereof.

According to one preferable embodiment of the present invention the base may be a combination of an inorganic base and an organic base, as defined above. The base may comprise 0.8-0.95 equivalent, preferably 0.9-0.95 equivalent, of an inorganic base and 0.05-0.2 equivalent, preferably 0.05-0.1 equivalent, of an organic base, given as molar equivalents. The inorganic and organic base may be added to the second reaction mixture, or separately but simultaneously, or separately and successively. Preferably the inorganic base is added first, followed by addition of organic base.

The second reaction mixture may preferably comprise water. Water may be introduced to the second reaction mixture together or after addition of base, preferably for example after addition of the inorganic and/or organic base. The water amount in the second reaction mixture may be 15-200 weight-%, preferably 40-150 weight-%, more preferably 55-100 weight-%, calculated from the amount of the inorganic base in the second reaction mixture. Efficient stirring of the second reaction mixture during the elimination reaction prevents the phase separation between the water and the low polarity solvent. The water content of the second reaction mixture enables a phase transfer process involving the organic base and inorganic base, if both present, that improves the efficiency of the base-catalyzed elimination reaction.

After the elimination reaction is complete, the compound according to Formula (I) is separated from the second reaction mixture. Usually a precipitate comprising organic and inorganic salts, such as copper salts, and the like. The precipitate may be easily separated from the organic solvent phase, e.g. by filtration. The compound according to Formula (I) remains in the organic solution phase of the second reaction mixture, formed by the low polarity solvent. The organic phase may be washed by using a mixture of sodium chloride and an organic acid, such as acetic acid or citric acid. A relatively pure compound according to Formula (I) may be obtained by removing the organic phase, e.g. by evaporation, whereby the compound according to Formula (I) is crystallized, and a solid or semi-solid product is obtained.

The term “comprises” as used throughout the description and claims herein means “includes or consists of”. The term denotes the inclusion of at least the features following the term and does not exclude the inclusion of other features which have not been explicitly mentioned. The term may also denote an entity which consists only of the features following the term.

EXPERIMENTAL

Embodiments of the invention are described more closely in the following non-limiting examples.

EXAMPLE 1

The following chemicals and reagents were used in the Example:

4-methylmorpholine, Sigma-Aldrich, purum >98%
methanesulfonic acid, Alfa Aesar, 98+%
copper(I) chloride, Alfa Aesar, 97%
acrylonitrile, Ineos, 99.4%
toluenesulfonyl chloride, Sigma-Aldrich, purum >98%.

The used chemicals and solvents methanol (MeOH), toluene, ethyl acetate (EtOAc), sodium carbonate, acetic acid, sodium chloride were reagent grade purity and obtained from commercial sources.

Step I: Preparation of the Ligand (4-methylmorpholinium hydromethanesulfonate, NMM*MsOH) for the Catalyst Complex 0.49 mol methanesulfonic acid, MsOH (20% solution in methanol) was added slowly to a stirred 0.5 mol solution of 4-methylmorpholine, NMM (20% solution in methanol) under cooling with cold water/ice. Temperature during the addition was kept under 40° C. After the addition of MsOH was completed, methanol was removed under reduced pressure on rotary evaporator and a yellowish oily residue was obtained. 80 ml of toluene was added to the residue and evaporated on rotary evaporator. Azeotropic drying was repeated with same amount of toluene. Evaporation was continued until the salt crystallizes. 4-methylmorpholinium hydromethanesulfonate, NMM*MsOH, was formed in quantitative yield.

Step II: Preparation of the Pre-Reaction Mixture 2.817 g CuCl (0.02756 mol), 8.337 g NMM*MsOH (0.04227 mol) prepared in Step I and 37.25 g acrylonitrile (0.702 mol) was charged in a 250 ml 1-neck round-bottom flask under nitrogen atmosphere. The pre-reaction mixture was stirred 0.5 h at room temperature under nitrogen atmosphere. Almost clear yellow-greenish solution of Cu(I)-complex with NMM and acrylonitrile was formed in 10-15 minutes.

Step III: Preparation of the First Reaction Mixture and Radical Addition Reaction. 3-[(4-Methylphenyl)sulfonyl]-2-chloropropanenitrile.

52.0 g toluenesulfonyl chloride (0.273 mol) was added in one portion to the pre-reaction mixture prepared in Step II. The obtained first reaction mixture was stirred about 0.5 h under nitrogen atmosphere. Temperature was raised to 88° C. during 1 h. Stirring and heating at 88° C. was continued overnight. The reaction flask was cooled to room temperature and the obtained intermediate product was analysed by thin layer chromatography, TLC (ethyl acetate:hexane 1:5).

Step IV: Preparation of the Second Reaction Mixture and the Elimination Reaction.

Acrylonitrile was removed from the first reaction mixture obtained in Step III under reduced pressure and 40 ml ethyl acetate was added in two portion and evaporated. This removed possible traces of acrylonitrile.

The intermediate product was dissolved in 150 g of ethyl acetate for forming a second reaction mixture. At this stage Cu(I) containing precipitate formed and was separated from the liquid phase by filtering. The liquid phase, i.e. the second reaction mixture was placed in 500 ml round-bottom flask. 13.07 g $Na_2CO_3$ was added under stirring, temperature 27° C. After addition of 6.7 ml of deionized water a slow gas evaluation started, temperature of the mixture was 28° C. 2.77 g NMM (10 mol-% of toluenesulfonyl chloride amount) was added in one portion. Temperature of the reaction mixture was 31° C. Samples for analysis with ultra performance liquid chromatography, UPLC were taken at time 0 min; 1 h 10 min; 2 h 30 min; 4 h 5 min; 6 h 15 min; 22 h 30 min. In the last sample, the content of E-3-[(4-methylphenyl)sulfonyl]-2-propenenitrile was 13.7 weight-% (79% yield from theoretical), no intermediate product was found.

Step V: Purification and Separation of the Desired Compound.

A yellow organic liquid phase was separated from semi-solid precipitate formed during elimination reaction by decanting. The precipitate was washed twice with 30 ml ethyl acetate. The ethyl acetate solutions were combined with the organic liquid phase. The combined organic phase was washed with three times with 20 ml (per time) washing solution comprising 50 g NaCl, 30 g acetic acid and 420 g deionized water and once with 10 ml DI-water. The washing was conducted by stirring on magnetic stirrer (500 rpm, 5 min).

After washing, the organic liquid phase was placed in a rotary evaporator and ethyl acetate was evaporated to dry. A reaction product crystallized during evaporation. 25 ml methanol was added to the crystallized reaction product and refluxed 0.5 h on water bath, cooled slowly to room temperature, and placed into fridge overnight (6° C.).

The product was filtered, washed with 50 ml of cold methanol and dried under reduced pressure on water bath (80-90° C.).

Yield 35.21 g, 62.5% from theoretical.

EXAMPLE 2

Step I: Preparation of the Ligand (4-methylmorpholinium toluenesulfonate, NMM*TosOH) for the Catalyst Complex 5.37 g of toluenesulphonic acid, TosOH*$H_2O$, (about 0.028 mol) was dissolved in 7 ml of MeOH. 2.93 g of N-methylmorpholine was added and resulted solution was evaporated to dry in a rotary evaporator with a water bath temperature of 90-95° C. A colourless crystalline salt was obtained at quantitative yield.

Step II: Preparation of the First Reaction Mixture and Radical Addition Reaction. 3-[(4-Methylphenyl)sulfonyl]-2-chloropropanenitrile.

In a 50 ml round bottom reaction flask was charged 265.2 mg CuCl (about 2.6 mmol), 1,1154 NMM*TosOH (about 4 mmol), 9.83 g toluene sulphonyl chloride, TosCl, (about 0.05 mol) and 9.09 g acrylonitrile (about 0.1715 mol).

The resulted clear yellowish-green reaction mixture was refluxed ($T_{set}$=88° C.) and magnetically stirred under $N_2$ for 16 h.

A conversion of TosCl of about 60% was achieved as measured by $H^1$ NMR, $CDCl_3$.

Unreacted acrylonitrile was evaporated using a rotary evaporator with a water bath at a temperature of 50-80° C. An oily product was formed. Ethyl acetate, EtOAc, (20 ml) was added and evaporation was repeated to remove residual acetonitrile.

Step III: Preparation of the Second Reaction Mixture and the Elimination Reaction.

The oily reaction product was dissolved in 50 ml EtOAc and transferred into a 100 ml round bottom reaction flask. 2.4 g of $Na_2CO_3$ (about 23 mmol), 4 ml of water and 0.5 ml of N-methylmorpholine (about 5 mmol) were added.

A yellowish reaction mixture was obtained. No crystalline product was observed in organic solution. The reaction mixture was stirred overnight at room temperature.

Next morning the organic phase was separated in a separation funnel. The water layer was washed twice with 15 ml of EtOAc. Combined organic phases were washed twice with 10 ml 1 wt % citric acid/10 wt % NaCl.

EtOAc was then evaporated using a rotary evaporator, 10 ml MeOH added and evaporation repeated. 10 ml MeOH was added, the mixture was refluxed without mixing and cooled slowly to room temperature.

The product was filtered, washed with 10 ml of cold MeOH and dried at 60-75° C. under reduced pressure (30-40 mbar). Colorless crystals were obtained.

Upon redissolution it was found that the product was 97.2% pure, with approximately 2.2% insolubles and 0.6% other impurities.

The above pure product was analysed by GC-MS. The purity of the sample was about 99.42% using this analytical method.

EXAMPLE 3 (COMPARATIVE)

Step I: Preparation of the First Reaction Mixture and Radical Addition Reaction. 3-[(4-Methylphenyl)Sulfonyl]-2-Chloropropanenitrile.

In a 100 ml round bottom reaction flask was charged 101.5 mg CuCl (about 1 mmol), 214.1 mg triethylamine chloride, $Et_3N$*HCl, (about 1.55 mmol), 19.19 g toluene sulphonyl chloride, TosCl, (about 0.1 mol) and 10.6 g acrylonitrile (about 0.2 mol).

The resulting clear yellowish reaction mixture was refluxed ($T_{set}$=88° C.) and magnetically stirred under $N_2$ for 16 h.

A conversion of TosCl of about 75% was achieved as measured by $H^1$ NMR, $CDCl_3$.

Unreacted acrylonitrile was evaporated using a rotary evaporator with a water bath at a temperature of 50-80° C.

An oily product was formed. Ethyl acetate, EtOAc, (30 ml) was added and evaporation was repeated to remove residual acetonitrile.

Step II: Preparation of the Second Reaction Mixture and the Elimination Reaction.

The reaction product was dissolved in 100 ml EtOAc and transferred into 250 ml round bottom reaction flask. 4.77 g of $Na_2CO_3$ (about 45 mmol), 6 ml of water and 1 ml of N-methylmorpholine (about 10 mmol) were added. A small amount of crystalline product was observed in organic solution. The solution was almost colorless. The reaction mixture was stirred overnight at room temperature.

Next morning the organic phase was separated in the separation funnel. The water layer was washed twice with 25 ml of EtOAc. Combined organic phases were washed twice with 10 ml 1 wt % citric acid/10 wt % NaCl. EtOAc was evaporated, 10 ml MeOH added and evaporation repeated. 25 ml MeOH was added, the mixture was refluxed without mixing and cooled slowly to room temperature.

The product was filtered, washed with 10 ml of cold MeOH and dried at 60-under reduced pressure (30-40 mbar). Colorless crystals were obtained.

Upon redissolution it was found that the product was 95.3% pure, with approximately 4.4% insolubles and 0.3% other impurities.

CONCLUSION

Comparative Example 3 was based on a catalyst complex containing relatively high amounts of chloride as a counterion with no organic sulphonate present. The addition reaction resulted in an intermediate product in which the organic phase contained some crystalline precipitate not observed in the corresponding Example 2 according to the invention. The elimination product of Comparative Example 3 was found to contain significantly more solids and other impurities after washing and recrystallisation.

It is possible that sulfonyl radical recombination products may arise in the Comparative Example. This may be the result of the use of a $Cl^-$ based catalyst where formation of polynuclear Cu-complexes with Cl-bridge atoms can arise. The use of organic sulfonates as counterions may resolve this issue and make possible uses of high loads of catalyst and even more robust synthesis methods.

The invention claimed is:

1. A method for preparing a compound of formula (I)

(I)

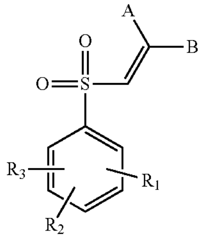

where

R1, R2, and R3 are independently selected from the group consisting of a hydrogen atom; a halogen atom; a hydroxy group, an alkyl group; a hydroxy alkyl group; a haloalkyl group;

an alkoxy group having 1 to 4 carbon atoms; an amino group; an alkylamino group or an acylamido group having 1 to 10 carbon atoms;

A is selected from the group consisting of a hydrogen atom; a C1-C5 alkyl group; or an alkoxycarbonyl group;

B is selected from the group consisting of a nitrile group; a carboxylic acid group, a carboxylic acid ester group or a carboxylic acid amide group;

the method comprising steps of (a) forming a first reaction mixture comprising a catalyst complex comprising Cu(I) and a ligand, wherein the ligand is selected from the group consisting of mono-, bi- or polydentate amine ligands;

an organic sulphonate counterion;

a reactive solvent selected from (meth)acrylonitrile or alkyl (meth)acrylate; and an aryl sulfonyl halide reactant;

(b) allowing a first reaction to proceed in the first reaction mixture at an elevated temperature, whereby an intermediate product is obtained;

(c) separating the unreacted reactive solvent from the first reaction mixture, and dissolving the intermediate product to a low polarity solvent to form a second reaction mixture;

(d) adding a base to the second reaction mixture, and allowing a second reaction to occur wherein the intermediate product undergoes a base-catalyzed elimination of the halogen atom from the intermediate product to form the compound according to Formula (I); and (e) separating the compound according to Formula (I) from the second reaction mixture.

2. The method according to claim 1, wherein the intermediate product is dissolved in step (d) into a low polarity solvent, which has a relative polarity of <0.4 to form the second reaction mixture.

3. The method according to claim 1, wherein the first reaction which is effected in step (b) is allowed to proceed at the elevated temperature of 80-95° C.

4. The method according to claim 1, wherein the reactive solvent, which is separated from the first reaction mixture in step (c), is recycled back to step (a) for formation of first reaction mixture.

5. The method according to claim 1, wherein the second reaction mixture in step (d) is maintained at a temperature of 15-40° C.

6. The method according to claim 1, wherein the base in step (d) comprises an inorganic base.

7. The method according to claim 1, wherein the base in step (d) comprises an organic base.

8. The method according to claim 1, wherein the base in step (d) is a combination of an inorganic base and an organic base, which comprises 0.8-0.95 equivalent of an inorganic base and 0.05-0.2 equivalent of an organic base, given as molar equivalents.

9. The method according to claim 1, wherein the amount of Cu(I) halide in the first reaction mixture is 2.5-30 mol-% calculated from the amount of the aryl sulphonyl halide in the first reaction mixture.

10. The method according to claim 1, wherein the organic sulphonate in step (a) comprises an aryl sulphonate or alkyl sulphonate.

11. The method according to claim 1, wherein the amount of the ligand in the first reaction mixture is 7-45 mol-%, calculated from the amount of the aryl sulphonyl halide in the first reaction mixture and/or wherein aryl sulphonyl halide is added, to form the first reaction mixture in step (a), in amount of 0.2-0.5 equivalents relative to the amount of the reactive solvent in the first reaction mixture.

12. The method according to claim 1, wherein step (a) comprises (i) forming a pre-reaction mixture comprising a catalyst complex of the Cu(I) and the ligand;

the organic sulphonate counterion; and a reactive solvent selected from (meth)acrylonitril e or alkyl (meth)acrylate; and (ii) adding an amount of aryl sulfonyl halide reactant to the pre-reaction mixture to form the first reaction mixture.

13. The method according to claim 1, wherein the compound according to formula (I) is 3-[(4-methylphenyl) sulphonyl]-2-propenenitrile.

14. The method according to claim 1, wherein the Cu (l) is provided as a Cu(I) halide.

15. The method according to claim 1, wherein the organic sulphonate is supplied as a salt.

16. The method according to claim 2, wherein the low polarity solvent is selected from the group consisting of ethyl acetate, butyl acetate, tetrahydrofuran, dioxane and toluene.

17. The method according to claim 1, wherein in step (d) the base is added to the second reaction mixture under cooling.

18. The method according to claim 3, wherein the first reaction in step (b) is allowed to proceed at the elevated temperature of 85-92° C.

19. The method according to claim 5, wherein the second reaction mixture in step (d) is maintained at a temperature of 20-35° C.

20. The method according to claim 6, wherein the base in step (d) comprises an inorganic base selected from the group consisting of bicarbonates or carbonates of alkali metals or carbonates of earth alkaline metals, or any mixtures thereof.

21. The method according to claim 7, wherein the base in step (d) comprises an organic base selected from the group consisting of triethylamine, trimethylamine; N-methylmorpholine; N-methylpyrrolidine; N,N-diisopropylethylamine; 1,4-diazabicyclo[2.2.2]-octane; 1,8-diazabicyclo[5.4.0]undec-7-ene; and 1,5-diazabicyclo[4.3.0]non-5-ene.

22. The method according to claim 9, wherein the amount of Cu(I) halide in the first reaction mixture is 5-20 mol-%, calculated from the amount of the aryl sulphonyl halide in the first reaction mixture.

23. The method according to claim 22, wherein the amount of Cu(I) halide in the first reaction mixture is 7.5-15 mol-%, calculated from the amount of the aryl sulphonyl halide in the first reaction mixture.

24. The method according to claim 10, wherein the organic sulphonate in step (a) comprises an aryl sulphonate or alkyl sulphonate which is selected from the group consisting of methanesulphonate, ethanesulphonate, benzenesulphonate, 4-toluenesulphonate, and xylenesulphonate.

25. The method according to claim 11, wherein the amount of the ligand in the first reaction mixture 10-30 mol-%, calculated from the amount of the aryl sulphonyl halide in the first reaction mixture and/or wherein aryl sulphonyl halide is added, to form the first reaction mixture in step (a), in an amount of 0.3-0.5 equivalents, relative to the amount of the reactive solvent in the first reaction mixture.

26. The method according to claim 12, wherein the pre-reaction mixture is formed at a temperature of 15-40° C.

27. The method according to claim 14, wherein the Cu(I) halide is a Cu(I) chloride.

28. The method according to claim 14, wherein the molar amount of halide ions in the first reaction mixture is no more than the molar amount of Cu(I).

29. The method according to claim 15, wherein the organic sulphonate is supplied as an ammonium salt.

* * * * *